US 8,242,312 B2

(12) United States Patent
Murphy et al.

(10) Patent No.: US 8,242,312 B2
(45) Date of Patent: Aug. 14, 2012

(54) URETHANE AND UREA FLUOROSURFACTANTS

(75) Inventors: Peter Michael Murphy, Chadds Ford, PA (US); Anilkumar Raghavanpillai, Wilmington, DE (US); Allison Mary Yake, Landenberg, PA (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 12/944,802

(22) Filed: Nov. 12, 2010

(65) Prior Publication Data

US 2012/0122999 A1    May 17, 2012

(51) Int. Cl.
*C07C 317/00* (2006.01)
*C07C 31/00* (2006.01)
*E21B 43/22* (2006.01)

(52) U.S. Cl. ............... 568/18; 568/300; 166/270.1
(58) Field of Classification Search .......... 568/18, 568/300; 166/270.1
See application file for complete search history.

(56) References Cited

U.S. PATENT DOCUMENTS

| | | | |
|---|---|---|---|
| 3,337,564 A | 8/1967 | Willmund | |
| 3,721,706 A | 3/1973 | Hoffman et al. | |
| 4,069,158 A | 1/1978 | Bertocchio et al. | |
| 4,099,574 A | 7/1978 | Cooper et al. | |
| 4,296,034 A | 10/1981 | Bouvet et al. | |
| 4,383,929 A * | 5/1983 | Bertocchio et al. | 252/8.05 |
| 4,460,791 A | 7/1984 | Cooke | |
| 4,472,286 A | 9/1984 | Falk | |
| 4,504,401 A | 3/1985 | Matsuo et al. | |
| 4,983,769 A | 1/1991 | Bertocchio et al. | |
| 5,516,459 A | 5/1996 | Van Eenam | |
| 5,616,273 A | 4/1997 | Clark et al. | |
| 5,672,673 A | 9/1997 | Kirchmeyer et al. | |
| 6,160,161 A | 12/2000 | Trabelsi et al. | |
| 6,201,122 B1 | 3/2001 | Dams | |
| 7,160,850 B2 | 1/2007 | Dams et al. | |
| 7,399,887 B1 | 7/2008 | Murphy et al. | |
| 7,638,650 B2 | 12/2009 | Qiu | |
| 2003/0171229 A1 | 9/2003 | Gonzalez | |
| 2003/0201419 A1 | 10/2003 | Tanaka et al. | |
| 2006/0142530 A1 | 6/2006 | Moore et al. | |

FOREIGN PATENT DOCUMENTS

| | | |
|---|---|---|
| DE | 1794356 A1 | 2/1973 |
| EP | 0856018 B1 | 10/2001 |
| GB | 1383378 A | 2/1974 |
| GB | 1566724 A | 5/1980 |
| GB | 1583363 A | 1/1981 |
| JP | 50059331 A | 5/1975 |
| JP | 50121183 A | 9/1975 |
| JP | 53009204 A | 1/1978 |
| JP | 53044154 A | 4/1978 |
| JP | 58038569 A | 3/1983 |
| JP | 58050971 A | 3/1983 |
| JP | 59230566 A | 12/1984 |
| JP | 60048131 A | 3/1985 |
| JP | 61100266 A | 5/1985 |
| JP | 60099272 A | 8/1985 |
| JP | 61191369 A | 8/1986 |
| JP | 1993018623 A | 1/1993 |
| JP | 2007252731 A | 10/2007 |

OTHER PUBLICATIONS

Honda et al., "Molecular Aggregation Structure and Surface Properties of Poly(fluoroalkyl acryiate) Thin Films", Macromolecules 2005, vol. 38, 5699-5705.
Jouani et al., "Synthesis Isocyanates of 2-F-Alkylethyl", Journal of Fluorine Chemistry, 1992, vol. 56, 85-92 (Abstract).
Lattimer et al., "The Use of Small-Scale Test Data to Characterized Some Aspects of Fire Fighting Foam for Suppression Modeling", Fire Safety Journal, vol. 38, 2003, 117-146.
Magrabi et al., "A Comparative Study of Drainage Characteristics in AFFF and FFFP Compressed-Air Fire-Fighting Foams", Fire Safety Journal vol. 37, 2002, 21-52.
NF, "Basics to Foam", Kidde Fire Fighting, 2001, pp. 1-1 to 1-7.
Vincenti et al., "Synthesis of Highly Fluorinated Chloroformates and Their Use as Derivatize Agents for Hydrophilic Compounds and Drinking-Water-Disinfection by Products", Helvetica Chimica ACTA, 2004, vol. 87, 373-375.
Jouani M A et al: Synthesis and Liposome Formation of New Snythetic Perfluoroalkylated Cationic Lipids Derived From N-002—(F-Alkyl) Ethylthio ¾ Methyl (or Propyl ¾ N'(2-Dimethylamindethyl) UREAS, Journal of Liposome Research, Taylor & Francis, Philadelphia, PA, US, Feb. 1, 1999, pp. 95-114. Szoni S et al.: "Bilayer formation in water from new urea-based double-chain dimethylammonium amphiphiles containing perfluorinated moletles", Trends in Colloid and Interface Science XIII: The 12th Conference of the European Colloid and Interface Society (ECIS 98), Dubrovnik, Croatia, Sep. 20-25, 1998, Springer, Berlin, Jan. 1, 1999, vol. 112, pp. 60-63.
Jouani, M.A. et al.: "Synthesis and aggregation properties of new fluorine-containing double-chain amphiphiles derived from di- and tri-substituted ureas", Supramolecular Science, vol. 2, No. 2, 1995, pp. 117-123.

* cited by examiner

*Primary Examiner* — Robert Havlin

(57) ABSTRACT

The present invention comprises a compound of a compound of Formula 1

$$R_f\text{–}C_nH_{2n}\text{–}X\text{–}\underset{O}{C}\text{–}Y\text{–}C_nH_{2n}O_m\text{–}\underset{R_2}{\overset{R_1}{N^+}}\text{–}R_3^-$$

Formula 1 wherein
$R_f$ is a $C_2$ to $C_{12}$ perfluoroalkyl optionally interrupted by one to four moieties each independently selected from the group consisting of —$CH_2$—, —O—, —S—, —S(O)—, and —S(O)$_2$—;
n is 1 to 6;
m is 0 to 2, provided that m is less than or equal to n.
X and Y are each independently O or NR,
R is hydrogen or $C_1$ to $C_6$ alkyl;
$R_1$, and $R_2$ are each independently $C_1$ to $C_6$ alkyl, optionally containing one or more oxygen atoms and may form a ring selected from the group of piperidine, pyrrolidine, and morpholine;
and
$R_3$ is O$^-$, $(CH_2)_pC(O)O^-$, $(CH_2)_pCH(OH)(CH_2)SO_3^-$, and $(CH_2)_qSO_3^-$;
p is 1 to 4; and q is 2 to 4 which is useful as a surfactant.

14 Claims, No Drawings

URETHANE AND UREA FLUOROSURFACTANTS

FIELD OF THE INVENTION

This invention relates to amphoteric urea and urethane fluorinated compounds and their use as surfactants to alter the surface behavior of a liquid.

BACKGROUND OF THE INVENTION

Fluorosurfactants are useful to provide surface effects, for example wetting, lowering surface tension, leveling, and foaming, in various applications such as coatings, floor finishes, cleaners, acid etching applications and oil field applications. Many commercially available surfactants contain perfluoroalkyl terminal chains. It is known in the art that as the length of fluorinated alkyl chains decrease, the performance characteristics of surface properties imparted to substrates treated therewith decrease as well. See Honda, et al., in "Molecular Aggregation Structure and Surface Properties of Poly(fluoroalkylacrylate) Thin Films" Macromolecules (2005), 38(13), 5699-5705. Honda et al. disclose that a perfluoroalkyl chain of at least 8 carbons is necessary to maintain the perfluoroalkyl chains in a parallel orientation. Shortening of the perfluoroalkyl chain, causes reorientation which results in a loss of performance.

Common fluorosurfactants are prepared through a fluorinated sulfonyl chloride intermediate. These intermediates are costly to produce and are in limited supply. Some preparations require a conversion of a fluorinated SCN moiety to a fluorinated $SO_2Cl$ moiety, which involves a reaction with gaseous chlorine, a very hazardous material. It is desirable to eliminate this reaction.

U.S. Pat. No. 4,383,929 discloses fluorinated sulphonobetaine compounds prepared from amines derived from fluorinated sulfonyl chloride intermediates. U.S. Pat. No. 6,201,122 discloses a fluoroaliphatic radical-containing sulfonamido anionic compound. These compounds are useful as anionic surfactants in liquids and are prepared through fluorinated sulfonyl chloride intermediates.

Additionally, precipitation is a known problem associated with anionic surfactants in some end use applications, such as oilfield applications. Precipitation causes degradation or complete loss of performance thus needs to be avoided.

It is desirable to have fluorosurfactant compounds with improved properties that can be produced from readily available fluorinated amines and alcohols without the need to use gaseous chlorine. Also desired is a method of altering the surface behaviors of liquids using these fluorosurfactant compounds which avoid precipitation problems. The present invention provides such compounds and methods.

SUMMARY OF THE INVENTION

The present invention comprises a compound of Formula 1

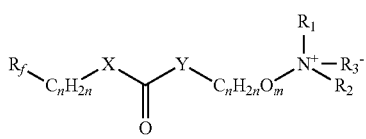

Formula 1 wherein
$R_f$ is a $C_2$ to $C_{12}$ perfluoroalkyl optionally interrupted by one to four moieties each independently selected from the group consisting of $—CH_2—$, $—O—$, $—S—$, $—S(O)—$, and $—S(O)_2—$;
n is 1 to 6;
m is 0 to 2, provided that m is less than or equal to n.
X and Y are each independently O or NR,
R is hydrogen or $C_1$ to $C_6$ alkyl;
$R_1$, and $R_2$ are each independently $C_1$ to $C_6$ alkyl, optionally containing one or more oxygen atoms and may form a ring selected from the group of piperidine, pyrrolidine, and morpholine;
and
$R_3$ is $O^-$, $(CH_2)_pC(O)O^-$, $(CH_2)_pCH(OH)(CH_2)SO_3^-$, and $(CH_2)_qSO_3^-$;
p is 1 to 4; and q is 2 to 4.

The present invention further comprises a method of altering the surface behavior of a liquid comprising contacting to the liquid a compound of Formula 1, or mixtures thereof, as defined above.

The present invention further comprises a method of altering the properties within a subterranean formation containing hydrocarbons comprising contacting the subterranean formation with a compound of Formula 1.

DETAILED DESCRIPTION

The present invention comprises a compound of Formula 1

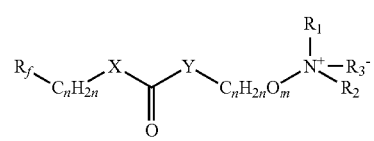

Formula 1 wherein
$R_f$ is a $C_2$ to $C_{12}$ perfluoroalkyl optionally interrupted by one to four moieties each independently selected from the group consisting of $—CH_2—$, $—O—$, $—S—$, $—S(O)—$, and $—S(O)_2—$;
n is 1 to 6;
m is 0 to 2, provided that m is less than or equal to n.
X and Y are each independently O or NR,
R is hydrogen or $C_1$ to $C_6$ alkyl;
$R_1$, and $R_2$ are each independently $C_1$ to $C_6$ alkyl, optionally containing one or more oxygen atoms and may form a ring selected from the group of piperidine, pyrrolidine, and morpholine;
and
$R_3$ is $O^-$, $(CH_2)_pC(O)O^-$, $(CH_2)_pCH(OH)(CH_2)SO_3^-$, and $(CH_2)_qSO_3^-$;
p is 1 to 4; and q is 2 to 4.

Preferred compounds of Formula 1 are those wherein $R_f$ is $C_4$ to $C_8$ perfluoroalkyl, more preferably those wherein $R_f$ is $C_4$ to $C_6$ perfluoroalkyl, more preferably $R_f$ is $C_4$ perfluoroalkyl. Preferred compounds of Formula 1 are those wherein that X and Y are not both oxygen. Also preferred are compounds of Formula 1 wherein n is 2 to 3, more preferably wherein n is 2 and m is 0. Also preferred are compounds of Formula 1 wherein $R_1$ and $R_2$ are $C_1$ to $C_2$ alkyl, and $R_3$ is $O^-$ or $(CH_2)_pC(O)O^-$.

Compounds of the present invention of Formula 1 are prepared through an intermediate of Formula 2:

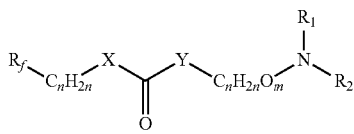

Formula 2 wherein $R_f$, n, m, X, Y, R, $R_1$, and $R_2$ are as defined above in Formula 1. Intermediate compounds of Formula 2 are quarternized to form compounds of Formula 1.

To produce compounds of Formula 1 with the specific formula

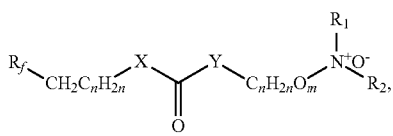

intermediates of Formula 2 are reacted with hydrogen peroxide at a temperature of about 50° C. for about 56 hours followed by a second addition of hydrogen peroxide and held for about an additional 12 hours. Further details of can be found in U.S. Pat. No. 4,983,769, herein incorporated by reference.

To produce compounds of Formula 1 with the specific formula

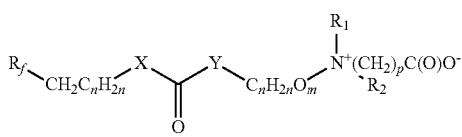

the intermediates of Formula 2 are reacted with a sodium salt of a chloro substituted acetic, proprionic, butanoic, or pentanoic acid at a temperature about 78° C. for about 24 hours. Further details can be found in U.S. Pat. No. 3,721,706, herein incorporated by reference.

To produce compounds of Formula 1 with the specific formula

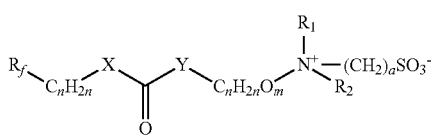

the intermediates of Formula 2 are reacted with a sodium salt of a chloro substituted ethanesulfonic acid, propanesulfonic acid or butanesulfonic acid at temperature of about 20° C. for about 30 minutes. Further details can be found in U.S. Pat. No. 4,383,929, herein incorporated by reference. These specific examples of Formula 1 can also be formed by reacting Formula 2 with a sulfone, for example ethane sulfone, propane sulfone, or butane sulfone.

Alternatively, the intermediates of Formula 2, can be reacted with 3-chloro-2-hydroxy-1-propanesulfonic acid sodium salt to produce compounds of Formula 1 with the specific formula

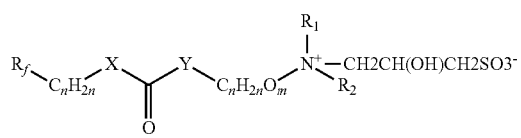

Reaction conditions can also be found in U.S. Pat. No. 4,383,929.

Intermediates of Formula 2 can be prepared by the reaction of an alcohol or amine with an isocyanate. Intermediates of Formula 2 can also be prepared from the reaction of a perfluorinated chloroformates with an amine. Specifically, compounds of Formula 2 are prepared by reacting fluoroalkyl alcohols with isocyanates, fluoroalkyl isocyanates with amino alcohols, or fluoroalkyl amines with isocyanates.

Urethane intermediates of Formula 2 having the specific formula

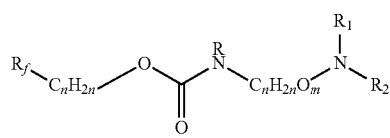

can be synthesized by reacting an isocyanate amine, preferably dimethylamino isocyanate, with a fluorinated alcohol of Formula 3

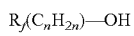

Formula 3 wherein Rf and n are as defined above in Formula 1. Fluorinated alcohols of Formula 3 are commercially available from E. I. Du Pont de Nemours and Company, Wilmington, Del.

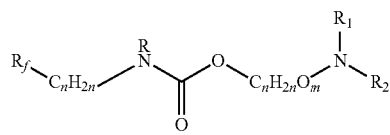

Urethane intermediates of Formula 2 having the specific formula can be synthesized by reacting an amino alcohol, preferably 3-dimethylamino-1-propanol, with a fluorinated isocyanate of Formula 4

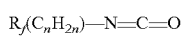

Formula 4 wherein Rf and n are as defined above in Formula 1. Compounds of Formula 4 are produced by first reacting fluoroalkyl iodides of formula $R_f(C_nH_{2n})I$ wherein $R_f$ and n as defined in Formula 1 and magnesium then dry ice ($CO_2$) followed by phosphorous pentachloride producing a fluoroalkyl acid chloride. The fluoroalkylethyl acid chloride is then reacted with sodium azide or trimethylsilylazide to form a fluorinated isocyanate.

Urea intermediates of Formula 2 having the specific formula

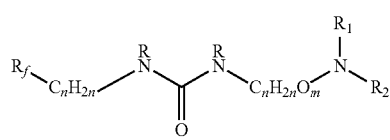

can be synthesized by reacting a fluorinated isocyanate of Formula 4 with a diamine, preferably dimethylamino alkyl amine, wherein Rf and n are as defined above.

Urea intermediates of Formula 2 having the specific formula

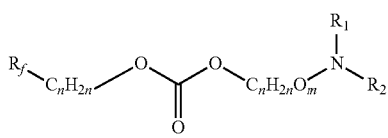

can be synthesized by reacting di substituted amino alkyl chloroformate, such as for example, dimethylamino ethyl chloroformate, with a fluorinated alcohol of Formula 3, as defined above.

The compounds of Formula 1 may further comprise water, one or more solvents, one or more surfactants, one or more additives, or combinations thereof. The compounds of Formula 1 can be in the form of foam, solution, or dispersion.

The compounds of Formula 1 are useful as surfactants and are capable of lowering surface tensions when added to aqueous media at low concentrations. These compounds are capable of lowering the surface tension of aqueous media to values less than about 25 milli-newtons per meter (mN/m), preferably less than about 20 milli-newtons per meter, at a concentration of the surfactant in the liquid of less than about 0.5% by weight, preferably less than 0.15% by weight.

The present invention provides several advantages. The compounds of Formula 1 are amphoteric and have excellent surfactant properties. They are stable in various formulations without precipitating out of solution, as demonstrated by the Examples herein. The compounds of Formula 1 contain a short terminal perfluoroalkyl chain of two to twelve carbons, preferably, two to six carbon atoms, and thus are less expensive than prior art compounds containing longer perfluoroalkyl chains, while providing the same or better surfactant properties. The compounds of Formula 1 can be manufactured without use of fluorinated sulfonyl chloride intermediates, and without the use of hazardous gaseous chlorine. Yet the compounds of Formula 1 perform comparably to commercial surfactants made using such fluorinated sulfonyl chloride intermediates.

In another embodiment, the present invention further comprises a method for altering the behavior of a liquid comprising adding to the liquid a compound of Formula 1, or a mixture thereof, wherein $R_f$, n, m, X, Y, R, $R_1$, and $R_2$ are as defined above in Formula 1. In this method of the present invention surface behaviors which are altered are selected from the group consisting of lowering surface tension, foaming, wetting, penetrating, spreading, leveling, flowing, emulsifying, dispersing, repelling, releasing, lubricating, etching, bonding, and stabilizing. Preferably, the altering of surface behavior is lowering the surface tension.

In the present embodiment, the method for altering the behavior of a liquid, the liquid is an emulsifying agent, foaming agent, release agent, repellency agent, flow modifier, film evaporation inhibitor, wetting agent, leveling agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor finish, or bonding agent. Addition methods where compounds of the present invention are useful can be found in U.S. Pat. Nos. 7,160,850; 7,399,887; and 7,638,650, which are herein incorporated by reference.

As previously noted the surface tension of aqueous media is lowered to values less than about 25 milli-newtons per meter (mN/m), preferably less than about 20 milli-newtons per meter, at a concentration of the surfactant in the liquid of less than about 0.5% by weight, preferably less than 0.15% by weight. The compounds of Formula 1 have a critical micelle concentration of less than about 0.2% by weight in water, preferably less than about 0.15%, more preferably less than about 0.1%, and more preferably less than about 0.05%. The surface tension beyond the critical micelle concentration in aqueous media is less than about 25 milli-newtons per meter, preferably less than about 20 milli-newtons per meter.

In another embodiment of the present invention the compounds of the present invention are useful in gas and oil field applications. The present invention comprises a method of altering the properties within a subterranean formation containing hydrocarbons comprising contacting the subterranean formation with a compound of Formula 1 as defined above.

Herein a "hydrocarbon" is either a gas or oil product which is produced or recovered from a subterranean zone. A well or well bore is drilled and created to penetrate such a hydrocarbon containing subterranean zone. The method of the present invention is useful to provide a surfactant or foaming agent to modify and improve the wettability and surface conditions, such as the surface tension of the subterranean formation around the well bore, and is also useful to improve the permeability and flow rate to enhance oil well or gas well recovery and productivity.

The term "drill fluids" as used herein means those liquids that are added to a well or well bore penetrating a subterranean zone containing hydrocarbon or gas prior to or during a drilling operation. Examples can include water, brine, solvent, hydrocarbons, surfactants, oils, kerosene, fracturing fluids, stimulating fluids, oil-based drill muds, clay stabilizers, treatment fluids, and mixtures thereof.

The term "well fluids" as used herein means those liquids that occur in or are added to a well or well bore penetrating a subterranean zone containing hydrocarbon or gas. Examples can include drill fluids, water, brine, solvent, hydrocarbons, surfactants, oils, kerosene, fracturing fluids, stimulating fluids, oil-based drill muds, clay stabilizers, treatment fluids, and mixtures thereof.

The term "liquid treatment stream or gas treatment stream" as used herein means a liquid composition or gas composition, or a combination thereof, injected into a well penetrating a subterranean zone containing hydrocarbon or gas, or into a well bore area, in the operation of extracting the hydrocarbon or gas. Examples can include steam, drill fluids, well fluids, stimulating fluids, water, brine, solvent, hydrocarbons, surfactants, fracturing fluids, oil-based drill muds, clay stabilizers, treatment fluids, and mixtures thereof.

The method of the present invention provides a compound of formula 1, which acts as a surfactant or foaming agent for oil field and gas field applications. In this embodiment the compound of formula 1 is typically used in an aqueous medium or solvent medium selected from the group consisting of water, saline solution, KCl solution, HCl solution, hydrocarbon, halocarbon, drill fluids, well fluids, liquid treatment stream, gas treatment stream, and a mixture thereof. The method of the present invention is useful to provide an additive in drill fluids, well fluids, and other treatment fluids for subterranean formations, to enhance gas or oil recovery by altering surface tension, wettability, or viscosity of the fluids, oils, condensates, and muds employed or encountered in such operations. The surfactant can be used for foaming porous rock or soil medium of a subterranean formation, or for other known well or well bore treatments.

The present invention provides a surfactant or foaming fluid which comprises the compounds of formula 1 and a medium, wherein the compound of formula 1 is present at a concentration range of from about 0.001% to about 50% by weight, preferably a range of from about 0.01% to about 30% by weight, and more preferably a range of from about 0.05% to about 20% by weight in the medium.

The present invention comprises a method of lowering the surface tension within a subterranean formation containing hydrocarbons comprising adding a compound of formula 1 as described above to a medium which is a carrier contacted with the subterranean formation. One method of contacting is injection of the carrier or medium into the subterranean formation, for example by using a downhole, well, or well bore. The compound of formula 1 is added to a carrier or medium such as a fluid or gas which will be in contact with the subterranean formation during operations to remove oil or gas from the formation. Examples include drill fluids, well fluids, stimulation fluids, liquid treatment stream, gas treatment stream, fractionating fluids, clay stabilizers, or other liquids or gases employed when extracting the hydrocarbons from the formation. The methods of the present invention employing compounds of formula 1 can be used in one or more of a pretreatment stage of injection of a pre-flush of various liquids, or in matrix or stimulation activities; in the main stage in various carrier fluids, or in a soaking of the formation for a specific time period; or in a post treatment stage for displacement operation to achieve better placement of the fluids containing the surfactant composition. The compound of Formula 1 is used in the media in the form of a liquid, emulsion, dispersion, or foaming agent.

Foaming is a desirable property of the surfactants used in the method of the present invention when used as additives to drill fluids, well fluids, and other fluids in oil and/or gas field applications for enhanced production and recovery. The aqueous or solvent based drilling fluids, well fluids, liquid or gas treatment streams, or other carrier compositions which contain the compound of formula 1 foam during drilling or well treatment processes, and therefore provide advantages for enhanced production and recovery. Examples of such advantages from the surfactant and foaming properties include aiding in the removal of fines from the well around the drill-bit and wellbore treatment area, and adjusting the permeability and wettability properties where the fluids contact around the drill-bit and wellbore treatment area. The addition of the surfactant using the method of the present invention boosts the foaming properties of the oil/gas well drilling fluids and treatment fluids. If these fines are not efficiently removed, they can result in damage to the drill-bit head, costing time and money to replace or repair.

Another advantage of contacting a subterranean formation containing hydrocarbons with the compounds of formula 1 as defined above is providing a method for stimulating production of hydrocarbons during operations to extract hydrocarbons from a subterranean formation. The method of the present invention employs the surfactant compounds of formula 1 as stimulation fluid additives for stimulation activities, such as hydraulic fracturing and acidizing. In these situations the stable foams of the surfactants improve the wetting of the stimulation fluid on the formation surface (rock) to allow for deeper penetration and better stimulation of the well bore region. The low surface tension of these additives permits the stimulation fluids to be more efficiently and easily recovered from downhole using the method of the present invention. As a result, the well will be able to more effectively produce gas and oil.

The method of the present invention is further useful to provide an aid to prevent and remedy water blocks or condensate blocks in wells and well bore areas. It is known that water can accumulate near the well bore of an oil or gas well and decrease productivity by decreasing the relative permeability of the oil or gas, which is called water block. In addition liquid hydrocarbons can also accumulate and cause a decrease in productivity in gas wells near or far from the well bore region known as condensate block. The compounds used in the method of the present invention can be used to help in removal of at least a portion of such accumulations of liquids in a water block or condensate block, or for reducing or preventing the formation of the accumulation of liquids in such blocks. The surfactant employed in the method of the present invention is useful as a surfactant additive in drill fluids, well fluids and treatment fluids for subterranean formation to alter the wettability and permeability by its surface active properties. Such surfactants, for example, are used within the porous rock medium of subterranean formation and can result in pressure changes or as foams can block the gas drain paths and result in the oil/gas recovery increases.

The compounds used in the method of the present invention can both create foam and maintain a stable foam in aqueous solution over a period of time. The degree of foaming and the time a stable foam is maintained are useful in various applications. Foaming is an important property of fluorosurfactants that are used as additives not only for drilling fluid additives for foaming and fluid additives for oilfield stimulations activities, but also for cleaners and etching solution processes. In cleaning solutions, foam is often used to promote adhesion of the active cleaning ingredient on the surface. In etching processes for the manufacture of electronic or photovoltaic components, it is undesirable to have additives that create foams sustainable over a long time period. These foams help to keep acid mists and vapors from venting off the etch bath.

The methods of the present invention have several uses and advantages as detailed above. The methods provide surface effects to media and substrates, such a lowering of surface tension, leveling and wetting, and foaming. The compounds of formula 1 employed in the methods of the present invention do not precipitate out of formulations commonly used in oilfield applications or other applications, such as acidic cleaners and acid etching solutions. The compounds employed in the methods of the present invention have a shorter terminal perfluoroalkyl group present, which is more economical than longer chain perfluoroalkyls due to the reduction in fluorine present, but still provide comparable or superior performance. Also the compounds of the present invention, and employed in the methods of the present invention can be prepared without the use of sulfonyl chloride intermediates, and without the use of hazardous gaseous chlorine.

Test Methods and Materials

The following test methods and materials (intermediates) were used in the Examples herein.

Test Methods

Test Method 1—Critical Micelle Concentration and Surface Tension Measurement

A stock solution was prepared in deionized water at 22° C. to 23° C. The stock solution was stirred until the solution reached equilibrium. The surface tension of the examples was measured via a Kruess Tensiometer, K11 Version 2.501, in accordance with instructions with the equipment. The Wilhelmy Plate method was used. A vertical plate of known perimeter was attached to a balance, and the force due to wetting was measured. Ten replicates were tested of each dilution, and the following machine settings were used: Plate Method SFT, 1.0 sec interval, 40.2 mm wetted length, 10 reading limit, 2 dynes/cm min Standard Deviation, and 9.80665 m/s$^2$ Gr. Acc. Lower surface tension indicated superior performance.

The critical micelle concentration (CMC) was defined as the concentration at which increased concentrations of surfactant essentially no longer reduce the surface tension. The CMC was determined by measuring the surface tension as described above as a function of surfactant concentration. Surface tension was then graphed (abscissa) versus log concentration (ordinate). The resulting curve had a nearly horizontal portion at concentrations higher than the CMC, and had a negative steep slope at concentrations less than the CMC. The CMC was interpreted as the concentration at the intersection of the extrapolated steep slope and the extrapolated near horizontal line. The Surface Tension beyond CMC was interpreted as the value in the flat portion of the curve. A lower CMC is desirable, as it indicates a lower cost for effective performance because less of the surfactant is required.

Test Method 2—Blender Foaming Test

The test procedure used to evaluate the foaming was a modified version of the blender foaming test ASTM D3519-88. A blender, graduated cylinder, glass sample bottles and a stop watch were employed. First, stock solutions of the testing base solutions were made. These solutions were hard water, tap water, de-ionized water, or artificial sea water. Samples of 100 mL of the fluorosurfactant at 0.1% active ingredient in the desired base testing solution were prepared and stirred overnight to ensure complete mixing. The blender was cleaned with de-ionized water, then acetone, and then de-ionized water again. Once clean, the blender was assembled for use. The test fluid sample of 100 mL was poured into the blender jar. The temperature of the test fluid was measured with a thermometer and recorded. The blender was then run for 20 seconds at 50-60% power. After 20 seconds, the liquid and foam were immediately poured into a 500 mL graduated cylinder. The initial liquid and foam height were measured in mL. The liquid and foam height were again measured at 5, 10 and 15 minutes. During this time, any observations of the foam were recorded such as its density or persistency. The blender foaming test was used to measure the amount of foam produced and the persistency of the foam. A difference in foam height of up to 10 mL is produced by variation in this method. Test results are listed in Table 3.

Materials

All materials are commercially available unless other noted.

1H,1H,2H,2H-perfluorooctyl chloroformate was prepared as described in Vincenti et al, "Synthesis of highly fluorinated chloroformates and their use as derivitizing agents for hydrophilic compounds and drinking0water-disinfection by-products", Helvetica Chimica Acta, 2004, 49(2), pp 370-375.

1H,1H,2H,2H-perfluorooctyl isocyanate was prepared by reacting 1H,1H,2H,2H-perfluorooctyl acid chloride with trimethylsilylazide as described in Jourani, et al, *J. Fluorine Chem.*, 1992, 56, pp 85-92.

1H,1H,2H,2H-perfluorooctyl acid chloride was prepared by reacting 1H,1H,2H,2H-perfluorooctyl iodide (commercially available from E. I. du Pont de Nemours and Company, Wilmington, Del.) with magnesium and dry ice followed by the addition of phosphorous pentachloride.

$C_6F_{13}CH_2CH_2SO_2NHCH_2CH_2CH_2N(CH_3)_2$ was prepared by reacting 1H,1H,2H,2H-perfluorooctyl sulfonyl chloride and dimethylaminopropylamine. 1H,1H,2H,2H-perfluorooctyl sulfonyl chloride was prepared by adding chlorine and acetic acid to 1H,1H,2H,2H-perfluorooctyl thiocyanate. 1H,1H,2H,2H-perfluorooctyl thiocyanate was prepared by reacting 1H,1H,2H,2H-perfluorooctyl iodide with potassium thiocyanate.

Intermediate 1

Intermediate 1 was prepared by mixing N,N-dimethyl-1,3-propanediamine (1.35 g, 13 mmols) with 1H,1H,2H,2H-perfluorooctyl chloroformate (4.0 g, 11 mmol) in hexane (100 mL) at 0° C. This mixture was stirred for 4 hours, then warmed to 23° C. and held for an additional 16 hours. The mixture was filtered to remove color solids. The filtrate was then washed with water four times to remove any amines. The filtrate was then dried over $MgSO_4$. Hexane was then rotoevaporated from the filtrate resulting in a pale, tan oil which was then characterized by GC/MS and $^1H$ NMR to be Intermediate 1, $C_6F_{13}CH_2CH_2OC(O)NHCH_2CH_2CH_2N(CH_3)_2$.

Intermediate 2

Intermediate 2 was prepared by mixing 1H,1H,2H,2H-perfluorooctyl isocyanate (10.2 g, 26.22 mmol), anhydrous dichloromethane (25 mL) and catalytic dibutyltin dilaurate (0.04 g, 0.06 mmol) and cooling to 10° C. This mixture was added dropwise to a solution of 3-(dimethylamino-)-1-propanol (2.7 g, 26.22 mmol). The resulting mixture was then warmed to ambient temperature and stirred for 12 hours. Solvents were removed by decanting from the oil layer. The oil layer was then dried under vacuum resulting in a brown oil and was then characterized by $^1H$ and $^{19}F$ NMR to be Intermediate 2, $C_6F_{13}CH_2CH_2NHC(O)OCH_2CH_2CH_2N(CH_3)_2$.

Intermediate 3

Intermediate 3 was prepared by adding mixture of 1H,1H,2H,2H-perfluorooctyl isocyanate (9.19 g, 23.6 mmol) in anhydrous dichloromethane (25 mL) and catalytic dibutyltin dilaurate (0.035 g, 0.056 mmol) to 3-(dimethylamino)-1-propylamine (2.41 g, 23.6 mmol) at 10° C. The reaction mixture was warmed to ambient temperature and stirred for 12 hours. Solvents were removed under vacuum. The resulting mixture was washed with two washes of hexane (5 mL each). The resulting mixture was decanted and dried under high vacuum to produce an oil. The oil was characterized by $^1H$ and $^{19}F$ NMR to be Intermediate 3, $C_6F_{13}CH_2CH_2NHC(O)NHCH_2CH_2CH_2N(CH_3)_2$.

EXAMPLES

Example 1

Example 1 was prepared by adding hydrogen peroxide (1.8 g, 35% w/w in water) to a solution of Intermediate 1 (5.0 g, 10.16 mmols) in ethanol (4.68 g). The mixture was heated at 50° C. for 16 hours. A small aliquot of manganese dioxide was used to quench any remaining peroxide. The mixture was then filtered to remove any solids. The filtrate was then standardized to a fluorinated solids concentration of 40% with deionized water. Filtrate was characterized by $^1H$ NMR to be Example 1, $C_6F_{13}CH_2CH_2OC(O)NHCH_2CH_2CH_2N(CH_3)_2{}^+O^-$. The example was tested for critical micelle concentration and surface tension in accordance with Test Method 1. The resulting data is in Table 1.

Example 2

Example 2 was prepared by adding chloroacetic acid sodium salt (1.86 g, 16.1 mmols) to a solution of Intermediate 1 (7.75 g, 15.8 mmols) in ethanol (26.0 g). The mixture was heated to 70° C. and held for 16 hours. The reaction mixture was then dried by nitrogen purge. The resulting solids were then dissolved in fresh ethanol (15.7 g). The solution was then filtered to remove sodium chloride. The remaining filtrate was then standardized to a 27% fluorinated solids concentration with deionized water. The product was characterized by $^1$H NMR to be Example 2, $C_6F_{13}CH_2CH_2OC(O)NHCH_2CH_2CH_2N(CH_3)_2{}^+CH_2C(O)O^-$. The example was tested for critical micelle concentration, surface tension, and foaming in accordance with Test Methods 1 and 2. The resulting data is in Tables 1 and 2.

Example 3

Example 3 was prepared by heating a solution of Intermediate 1 (2.98 g, 6.046 mmol) in ethanol (2.8 g) and water (1.7) to 80° C. 3-Chloro-2-hydroxy-1-propanesulfonic acid sodium salt (1.3 g, 6.5 mmol) and CELITE 454 (0.103 g) were then added to the solution. The reaction was held at 80° C. for 12 hours. The reaction mixture was then filtered hot to remove any reaction solids. The filtrate was standardized to 27% fluorinated solids with deionized water. The product was characterized by $^1$H NMR to be Example 3, $C_6F_{13}CH_2CH_2OC(O)NHCH_2CH_2CH_2N(CH_3)_2{}^+CH_2CH(OH)CH_2SO_3{}^-$. The example was tested for critical micelle concentration and surface tension in accordance with Test Method 1. The resulting data is in Table 1.

Example 4

Example 4 was prepared by adding sodium chloroacetate (0.64 g, 5.58 mmol) and CELITE 545 to a solution of Intermediate 2 (2.5 g, 5.0 mmol) dissolved in ethanol (1.86 g, 40.6 mmol) and water (0.07 g) at ambient temperature. The mixture was heated to 75° C. and refluxed for 12 hours. The mixture was then cooled and filtered to remove any reaction solids. The solids were washed with hot ethanol (5 mL) and added to the previous filtrate. The solvents were removed by high vacuum resulting in a thick oil. The product was characterized by NMR to be Example 4, $C_6F_{13}CH_2CH_2NHC(O)OCH_2CH_2CH_2N(CH_3)_2{}^+CH_2C(O)O^-$. The example was tested for critical micelle concentration and surface tension in accordance with Test Method 1. The resulting data is in Table 1.

Example 5

Example 5 was prepared by adding 3-chloro-2-hydroxypropanesulfonic acid sodium salt (2.0 g, 4.06 mmol) and CELITE 545 to a solution of Intermediate 2 (2.0 g, 4.06 mmol) in ethanol (1.86 g, 40.6 mmol) and water (0.07 g) at ambient temperature. The mixture was heated to 75° C. and refluxed for 12 hours. The mixture was then cooled and filtered to remove any reaction solids. The solids were washed with hot ethanol (5 mL) and added to the previous filtrate. The solvents were removed by high vacuum resulting in a thick, brown oil. The product was characterized by NMR to be Example 5, $C_6F_{13}CH_2CH_2NHC(O)OCH_2CH_2CH_2N(CH_3)_2{}^+CH_2CH(OH)CH_2SO_3{}^-$. The example was tested for critical micelle concentration and surface tension in accordance with Test Method 1. The resulting data is in Table 1.

Example 6

Example 6 was prepared by adding sodium chloroacetate (0.64 g, 5.58 mmol) and CELITE 545 to a solution of Intermediate 3 (2.5 g, 5.08 mmol) at ambient temperature. The mixture was then heated to 75° C. and refluxed for 12 hours. The mixture was then cooled and the mixture was vacuumed filtered through a fritted filter to remove reaction solids. The solids were washed with hot ethanol (5 mL), which was added to the filtrate. The solvents were removed under high vacuum resulting in a pale yellow solid. The solids were characterized by NMR to be Example 6, $C_6F_{13}CH_2CH_2NHC(O)NHCH_2CH_2CH_2N(CH_3)_2{}^+CH_2C(O)O^-$. The example was tested for critical micelle concentration and surface tension in accordance with Test Method 1. The resulting data is in Table 1.

Example 7

Example 7 was prepared by adding 3-chloro-2-hydroxypropanesulfonic acid sodium salt (0.925 g, 4.47 mmol) to Intermediate 3 (2.0 g, 4.06 mmol) at ambient temperature. The mixture was then heated to 75° C. and refluxed for 12 hours. The mixture was then cooled and the mixture was vacuumed filtered through a fritted filter to remove reaction solids. The solids were washed with hot ethanol (5 mL), which was added to the filtrate. The solvents were removed under high vacuum resulting in an off white solid. The solids were characterized by NMR to be Example 7, $C_6F_{13}CH_2CH_2NHC(O)NHCH_2CH_2CH_2N(CH_3)_2{}^+CH_2CH(OH)CH_2SO_3{}^-$ The example was tested for critical micelle concentration and surface tension in accordance with Test Method 1. The resulting data is in Table 1.

Comparative Example A

Comparative Example A was prepared according to the process of Example 1 by substituting $C_6F_{13}CH_2CH_2SO_2NHCH_2CH_2CH_2N(CH_3)_2$ for Intermediate 1. The filtrate was characterized by $^1$H NMR to be Comparative Example A, $C_6F_{13}CH_2CH_2SO_2NHCH_2CH_2CH_2N(CH_3)_2{}^+O^-$. The example was tested for critical micelle concentration and surface tension in accordance with Test Method 1. The resulting data is in Table 1.

Comparative Example B

Comparative Example B was prepared according to the process of Example 2 by substituting $C_6F_{13}CH_2CH_2SO_2NHCH_2CH_2CH_2N(CH_3)_2$ for Intermediate 1. The filtrate was characterized by $^1$H NMR to be Comparative Example B, $C_6F_{13}CH_2CH_2SO_2NHCH_2CH_2CH_2N(CH_3)_2{}^+CH_2C(O)O^-$. The example was tested for critical micelle concentration, surface tension, and foaming in accordance with Test Methods 1 and 2. The resulting data is in Tables 1 and 2.

Comparative Example C

Comparative Example C was prepared according to the process of Example 3 by substituting $C_6F_{13}CH_2CH_2SO_2NHCH_2CH_2CH_2N(CH_3)_2$ for Intermediate 1. The filtrate was characterized by $^1$H NMR to be Comparative Example C, $C_6F_{13}CH_2CH_2SO_2NHCH_2CH_2CH_2N(CH_3)_2{}+CH_2CH(OH)CH_2SO_3{}^-$. The example was tested for critical micelle concentration and surface tension in accordance with Test Method 1. The resulting data is in Table 1.

TABLE 1

Critical Micelle Concentration and Surface Tension

| Example | Critical Micelle Concentration, CMC (% w/w) | Surface Tension beyond CMC (mN/m) |
|---|---|---|
| 1 | 0.0040 | 16.1 |
| 2 | 0.024 | 19.0 |
| 3 | 0.010 | 14.8 |
| 4 | 0.0050 | 18.6 |
| 5 | 0.12 | 19.1 |
| 6 | 0.020 | 18.6 |
| 7 | 0.0083 | 14.8 |
| Comparative Example A | 0.013 | 15.6 |
| Comparative Example B | 0.013 | 16.4 |
| Comparative Example C | 0.0065 | 17.3 |

The normal surface tension of deionized water is 72 dyne/cm ($72 \times 10^{-4}$ mN/m). The data in Table 1 demonstrated that Examples 1 to 7 when added to water, reduced the surface tension significantly. Compounds of this invention of Examples 1 to 7 performed as well in reducing surface tension of water, and were comparable or better than the commercially available surfactants of the Comparative Examples.

TABLE 2

Foaming

| | Foam Volume (mL) | | | |
|---|---|---|---|---|
| | Initial | t = 5 min | t = 10 min | t = 15 min |
| Tap Water: | | | | |
| Example 2 | 295 | 230 | 209 | 200 |
| Comparative Example B | 220 | 130 | 123 | 120 |
| 10% NaCl: | | | | |
| Example 2 | 255 | 188 | 169 | 162 |
| Comparative Example B | 225 | 160 | 140 | 135 |

The data in Table 2 showed that Example 2 demonstrated a significant improvement in initial foam formation and sustainable foam over the 15 minute test period compared to Comparative Example B in both tap water and 10% NaCl solution.

What is claimed is:

1. A compound of Formula 1

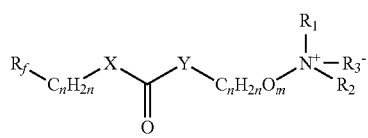

Formula 1 wherein $R_f$ is a $C_2$ to $C_{12}$ perfluoroalkyl optionally interrupted by one to four moieties each independently selected from the group consisting of —$CH_2$—, —O—, —S—, —S(O)—, and —S(O)$_2$—;

each n is 1 to 6;

m is 0 to 1, provided that m is less than or equal to n;

X and Y are each independently O or NR,

R is hydrogen or $C_1$ to $C_6$ alkyl;

$R_1$, and $R_2$ are each independently $C_1$ to $C_6$ alkyl, optionally containing one or more oxygen atoms and may form a ring selected from the group of piperidine, pyrrolidine, and morpholine;

and $R_3$ is O$^-$, $(CH_2)_pC(O)O^-$, $(CH_2)_pCH(OH)(CH_2)SO_3^-$, and $(CH_2)_qSO_3^-$;

p is 1 to 4; and q is 2 to 4.

2. The compound of claim 1 wherein $R_f$ is a $C_2$ to $C_6$ perfluoroalkyl.

3. The compound of claim 1 wherein $R_3$ is O$^-$ or $(CH_2)_pC(O)O^-$.

4. The compound of claim 1 having a surface tension beyond critical micelle concentration of about 20 mN/m or less.

5. The compound of claim 1 in the form of a foam.

6. The compound of claim 1 in the form of a solution or dispersion.

7. The compound of claim 6 further comprising water or solvent.

8. The compound of claim 6 further comprising one or more surfactants.

9. A method of altering the surface behavior of a liquid comprising adding to the liquid the compound of Formula 1 or a mixture thereof:

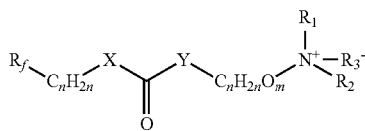

Formula 1 wherein $R_f$ is a $C_2$ to $C_{12}$ perfluoroalkyl optionally interrupted by one to four moieties each independently selected from the group consisting of —$CH_2$—, —O—, —S—, —S(O)—, and —S(O)$_2$—;

each n is 1 to 6;

m is 0 to 1, provided that m is less than or equal to n;

X and Y are each independently O or NR,

R is hydrogen or $C_1$ to $C_6$ alkyl;

$R_1$, and $R_2$ are each independently $C_1$ to $C_6$ alkyl, optionally containing one or more oxygen atoms and may form a ring selected from the group of piperidine, pyrrolidine, and morpholine;

and $R_3$ is O$^-$, $(CH_2)_pC(O)O^-$, $(CH_2)_pCH(OH)(CH_2)SO_3^-$, and $(CH_2)_qSO_3^-$;

p is 1 to 4; and q is 2 to 4.

10. The method of claim 9 wherein the altering the surface behavior is lowering the surface tension.

11. The method of claim 9 wherein the surface behavior is selected from the group consisting of foaming, wetting, penetration, spreading, leveling, flowing, emulsifying, dispersing, repelling, releasing, lubricating, etching, bonding, and stabilizing.

12. The method of claim 9 wherein the liquid is a coating composition, latex, polymer, floor finish, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, floor finish, or bonding agent.

13. A method of altering the properties within a subterranean formation containing hydrocarbons comprising contacting the subterranean formation with a compound of claim 1.

14. The method of claim 13 wherein the property altered is selected from the group consisting of lowering of the surface tension, removal of fines around a drill bit, changing the permeability or wettability of the formation, reducing the viscosity of the formation, stimulating production of hydrocarbons, and preventing or remedying water or condensate blocks in the formation.

* * * * *